US00PP19494P2

(12) United States Plant Patent
Lubbe

(10) Patent No.: US PP19,494 P2
(45) Date of Patent: Nov. 25, 2008

(54) ***ECHINACEA* PLANT NAMED 'MOUNT HOOD'**

(50) Latin Name: *Echinacea purpurea*
Varietal Denomination: Mount Hood

(75) Inventor: Remy Lubbe, Noordwijkherhout (NL)

(73) Assignee: Molter B.V., Noordwijkherhout (NL)

( * ) Notice: Subject to any disclaimer, the term of this patent is extended or adjusted under 35 U.S.C. 154(b) by 0 days.

(21) Appl. No.: 11/978,494

(22) Filed: Oct. 29, 2007

(51) Int. Cl.
*A01H 5/00* (2006.01)

(52) U.S. Cl. ..... Plt./428

(58) Field of Classification Search ..... Plt./428
See application file for complete search history.

*Primary Examiner*—Kent L. Bell
(74) *Attorney, Agent, or Firm*—C. A. Whealy

(57) ABSTRACT

A new and distinct cultivar of *Echinacea* plant named 'Mount Hood', characterized by its upright and bushy plant habit; freely flowering habit; inflorescences with white-colored ray florets subtending the receptacle and also developing at the apex of the receptacle; strong flowering stems that hold the inflorescences upright; and good garden performance.

2 Drawing Sheets

Botanical designation: *Echinacea purpurea.*
Cultivar denomination: 'Mount Hood'.

BACKGROUND OF THE INVENTION

The present invention relates to a new and distinct cultivar of *Echinacea* plant, botanically known as *Echinacea purpurea,* and hereinafter referred to by the name 'Mount Hood'.

The new *Echinacea* is a naturally-occurring whole plant mutation of the *Echinacea purpurea* cultivar Double Decker, not patented. The new *Echinacea* was discovered and selected by the Inventor as a single flowering plant from within a population of plants of the cultivar Double Decker grown in a controlled environment in Noordwijkerhout, The Netherlands during the summer of 2004.

Asexual reproduction of the new *Echinacea* by micropropagation since the autumn of 2004 in a controlled environment in Noordwijkerhout, The Netherlands has shown that the unique features of this new *Echinacea* are stable and reproduced true to type in successive generations.

SUMMARY OF THE INVENTION

The cultivar Mount Hood has not been observed under all possible environmental conditions. The phenotype may vary somewhat with variations in environment such as temperature and light intensity, without, however, any variance in genotype.

The following traits have been repeatedly observed and are determined to be the unique characteristics of 'Mount Hood'. These characteristics in combination distinguish 'Mount Hood' as a new and distinct cultivar of *Echinacea:*

1. Upright and bushy plant habit.
2. Freely flowering habit.
3. Inflorescences with white-colored ray florets subtending the receptacle and also developing at the apex of the receptacle.
4. Strong flowering stems that hold the inflorescences upright.

5. Good garden performance.

Compared to plants of the parent, the cultivar Double Decker, plants of the new *Echinacea* differ primarily in ray floret color as plants of the cultivar Double Decker have pink-colored ray florets.

Plants of the new *Echinacea* can be compared to plants of the *Echinacea* cultivar Alaska, disclosed in U.S. Plant Pat. No. 17,547. Plants of the new *Echinacea* differed primarily from plants of the cultivar Alaska in inflorescence form as plants of the cultivar Alaska do not develop ray florets at the apex of the receptacle.

BRIEF DESCRIPTION OF THE PHOTOGRAPHS

The accompanying photographs illustrate the overall appearance of the new *Echinacea.* The photographs show the colors as true as it is reasonably possible to obtain in colored reproductions of this type. Colors in the photographs may differ slightly from the color values cited in the detailed botanical description which accurately describe the colors of the new *Echinacea.*

The photograph on the first sheet comprises a side perspective view of a typical plant of 'Mount Hood' just before flowering grown in an outdoor nursery.

The photograph on the second sheet is a close-up view of a typical open inflorescence of 'Mount Hood'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in Noordwijkerhout, The Netherlands during the spring and summer in an outdoor nursery and under conditions and practices which approximate those generally used in commercial *Echinacea* production. During the production of the plants, day temperatures ranged from 18° C. to 22° C. and night temperatures ranged from 10° C. to 16° C. Measurements and numerical values represent averages for typical flowering plants. Plants were about two years old when the photographs and description were taken.

Botanical classification: *Echinacea purpurea* cultivar Mount Hood.

Parentage: Naturally-occurring whole plant mutation of the *Echinacea purpurea* cultivar Double Decker, not patented.

Propagation:

*Type.*—By micropropagation.

*Time to initiate roots.*—About three weeks at 15° C. to 20° C.

*Root description.*—Medium in thickness, fleshy; color, 162C.

*Rooting habit.*—Freely branching; moderately dense.

Plant description:

*Plant form/growth habit.*—Upright and bushy plant habit; freely branching habit with about eight lateral branches per plant; terminal inflorescences held upright on strong peduncles. Moderately vigorous growth habit.

*Plant height.*—About 70 cm.

*Plant diameter or spread.*—About 40 cm.

*Lateral branches.*—Length: About 30 cm. Diameter: About 6 mm. Internode length: About 8 cm. Aspect: Upright. Strength: Strong. Texture: Pubescent. Color: 146B.

Foliage description:

*Arrangement.*—Alternate, simple; sessile.

*Length.*—About 20 cm.

*Width.*—About 5 cm.

*Shape.*—Lanceolate.

*Apex.*—Acuminate.

*Base.*—Cordate.

*Margin.*—Entire.

*Texture, upper and lower surfaces.*—Pubescent; rough.

*Venation pattern.*—Pinnate.

*Color.*—Developing foliage, upper surface: 146A. Developing foliage, lower surface: 147B. Fully expanded foliage, upper surface: 137A; venation, 147A. Fully expanded foliage, lower surface: 147B; venation, 139B.

Inflorescence description:

*Appearance.*—Rotate composite inflorescence form with ray florets subtending and also developing at the apex of the receptacle. Freely flowering habit, about 25 inflorescences develop per plant. Inflorescences mostly terminal; occasional axillary inflorescence development at upper leaf axils; inflorescences held upright on strong peduncles. Inflorescences persistent.

*Fragrance.*—None detected.

*Time to flower.*—Plants flower continuously from July through August in The Netherlands.

*Inflorescence longevity.*—Inflorescences maintain good substance for about six weeks on the plant.

*Inflorescence bud.*—Height: About 1.5 cm. Diameter: About 2 cm. Shape: Conical. Color: 137D.

*Inflorescence size.*—Diameter: About 4 cm. Depth (height): About 5 cm to 7 cm. Disc Diameter: About 1 cm. Receptacle height: About 8 mm to 10 mm. Receptacle diameter: About 8 mm to 10 mm.

*Ray florets.*—Length: About 5 cm. Width: About 1 cm. Shape: Lanceolate. Apex: Acute. Base: Attenuate; fused into a short corolla tube. Texture, upper and lower surfaces: Smooth, glabrous. Number of ray florets subtending the receptacle: About 40 arranged in one or two whorls. Number of ray florets arising from the apex of the receptacle: About 80 massed together in numerous whorls. Aspect, lower florets: Horizontal to drooping. Aspect, upper florets: Upright. Color: When opening, upper and lower surfaces: Close to 155C. Fully opened, upper surface: Close to 155C. Fully opened, lower surface: Close to 157B.

*Disc florets.*—Shape: Tubular; apex five-pointed. Length: About 5 mm. Diameter: About 2 mm. Number of disc florets per inflorescence: About 120. Texture: Smooth, glabrous. Color: Immature: Apex, 144C; mid-section, 141C; base, 155A. Mature: Apex, 17B; mid-section, 141C; base, 155A.

*Receptacle spines.*—Quantity: One per disc floret. Length: About 5 mm to 7 mm. Width: About 2 mm to 3 mm. Shape: Acicular. Apex: Sharply acute. Base: Tapering. Texture: Smooth, glabrous. Color: 17B.

*Phyllaries.*—Quantity per inflorescence: About four to six in a single whorl. Length: About 8 mm to 10 mm. Width: About 2 mm. Shape: Lanceolate. Apex: Acuminate. Base: Truncate. Margin: Entire. Texture, upper and lower surfaces: Pubescent. Color, upper and lower surfaces: 137A.

*Reproductive organs.*—Androecium: Stamens per disc floret: One. Filament length: About 3 mm. Filament color: 199B. Anther shape: Rounded. Anther length: About 8 mm. Anther color: 145A. Pollen amount: Moderate. Pollen color: 162C. Gynoecium: Pistil length: About 3 mm. Stigma shape: Bi-parted. Stigma color: 149C. Style length: About 4 mm. Style color: 149C. Ovary color: 149C.

*Seeds/fruits.*—Seed and fruit development has not been observed.

Disease/pest resistance: Plants of the new *Echinacea* have not been shown to be resistant to pathogens and pests common to *Echinacea*.

Garden performance: Plants of the new *Echinacea* have been observed to have good garden performance and to tolerate rain, wind and temperatures from about −20° C. to about 35° C.

It is claimed:

1. A new and distinct *Echinacea* plant named 'Mount Hood' as illustrated and described.

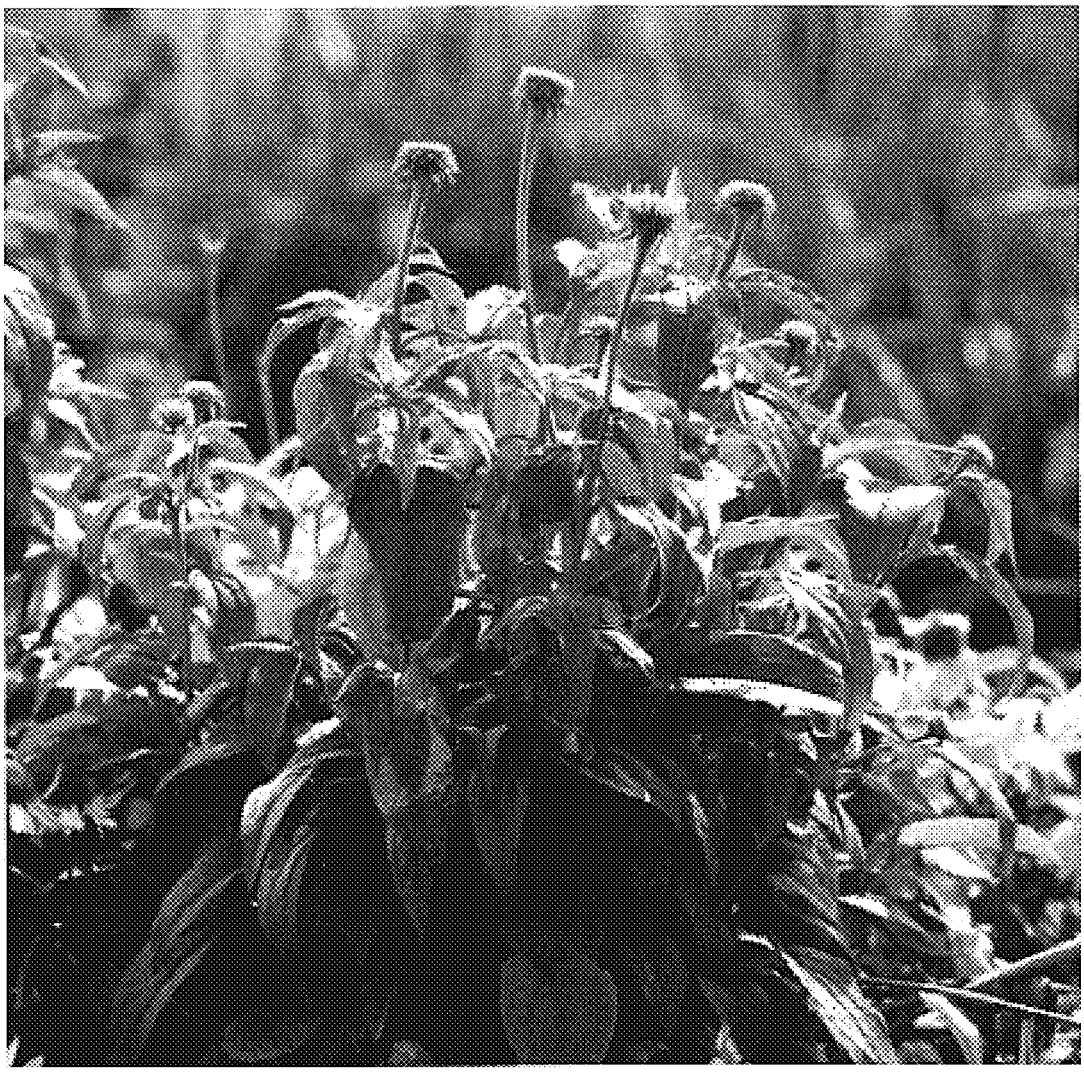

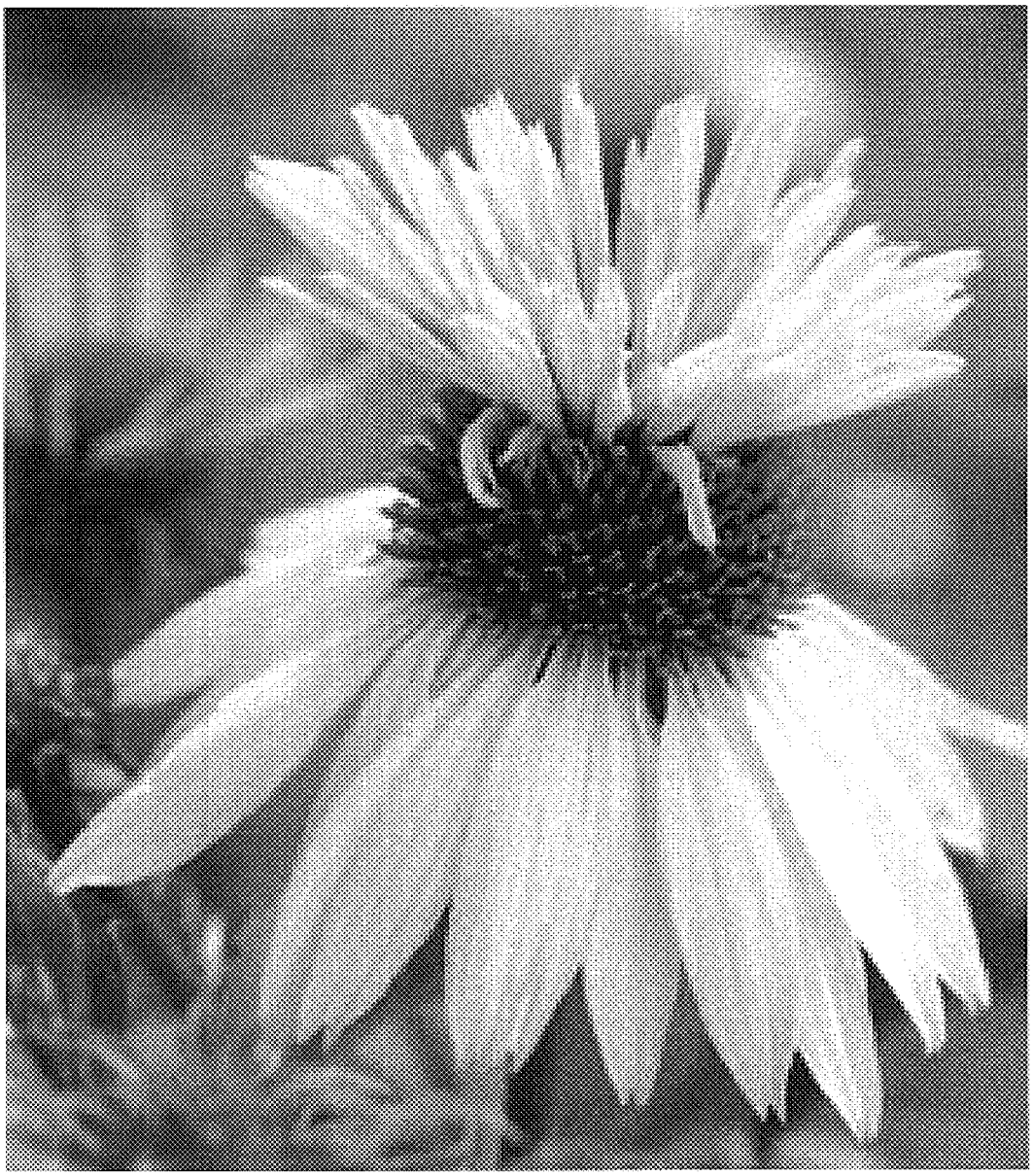

* * * * *